United States Patent [19]

Sauer et al.

[11] Patent Number: 5,690,669
[45] Date of Patent: Nov. 25, 1997

[54] APPARATUS FOR EXPANDING BODY TISSUE

[75] Inventors: Jude S. Sauer; James W. Kaufer, both of Pittsford; Daniel E. McGarry, North Chili; John F. Hammond, Canandaigua, all of N.Y.

[73] Assignee: Laser Surge, Inc., Rochester, N.Y.

[21] Appl. No.: 592,056

[22] Filed: Jan. 26, 1996

[51] Int. Cl.$^6$ ............................................ A61M 29/00
[52] U.S. Cl. ............................ 606/196; 606/192; 604/96
[58] Field of Search .................................. 606/191–198; 604/96, 97, 98, 103

[56] References Cited

U.S. PATENT DOCUMENTS

| | | |
|---|---|---|
| 4,278,081 | 7/1981 | Jones . |
| 4,324,235 | 4/1982 | Beran . |
| 4,340,046 | 7/1982 | Cox . |
| 4,364,391 | 12/1982 | Toye . |
| 4,449,523 | 5/1984 | Szachowicz et al. ............... 128/200.26 |
| 4,459,984 | 7/1984 | Liegner ............................. 128/207.15 |
| 4,471,776 | 9/1984 | Cox .................................. 128/207.15 |
| 4,573,460 | 3/1986 | Szachowicz et al. ............... 128/200.26 |
| 4,677,978 | 7/1987 | Melker ............................. 128/207.14 |
| 4,877,021 | 10/1989 | Higer et al. ...................... 128/200.76 |
| 5,045,061 | 9/1991 | Seifert et al. ..................... 604/96 |
| 5,054,484 | 10/1991 | Hebeler, Jr. ...................... 128/207.16 |
| 5,056,515 | 10/1991 | Abel ................................ 128/207.15 |
| 5,058,580 | 10/1991 | Hazard ............................. 128/207.15 |
| 5,062,420 | 11/1991 | Levine ............................. 128/204.18 |
| 5,087,246 | 2/1992 | Smith .............................. 604/96 |
| 5,090,408 | 2/1992 | Spofford et al. ................... 128/207.14 |
| 5,181,509 | 1/1993 | Spofford et al. ................... 128/207.14 |
| 5,186,168 | 2/1993 | Spofford et al. ................... 128/207.29 |
| 5,188,630 | 2/1993 | Christoudias ...................... 606/191 |
| 5,209,731 | 5/1993 | Sterman et al. .................... 604/97 |
| 5,217,005 | 6/1993 | Weinstein ......................... 128/200.26 |
| 5,217,007 | 6/1993 | Ciaglia ............................ 128/207.29 |
| 5,217,008 | 6/1993 | Lindholm ......................... 128/207.14 |
| 5,235,970 | 8/1993 | Augustine ........................ 128/200.26 |
| 5,279,285 | 1/1994 | Griggs ............................. 128/200.26 |
| 5,290,306 | 3/1994 | Trotta et al. ...................... 604/96 |
| 5,304,147 | 4/1994 | Johnson et al. ................... 604/183 |
| 5,306,147 | 4/1994 | Dragan et al. .................... 433/90 |
| 5,314,443 | 5/1994 | Rudnick .......................... 604/96 |
| 5,322,062 | 6/1994 | Servas ............................. 128/207.14 |
| 5,336,201 | 8/1994 | Von Der Decken ................ 604/223 |
| 5,352,206 | 10/1994 | Cushieri et al. .................. 604/164 |
| 5,370,615 | 12/1994 | Johnson .......................... 604/96 |
| 5,370,618 | 12/1994 | Leonhardt ........................ 604/96 |

OTHER PUBLICATIONS

Abbrecht, Peter H., MD, PhD, et al.; Insertion Forces and Risk of Complications During Cricothyroid Cannulation; The Journal of Emergency Medicine, vol. 10, pp. 417–426; 1992 Pergamon Press Ltd. USA.

*Primary Examiner*—Michael Buiz
*Assistant Examiner*—Patrick W. Rasche
*Attorney, Agent, or Firm*—Cumpston & Shaw

[57] ABSTRACT

A surgical apparatus for manipulating body tissue includes a handle member consisting of a frame, a self contained fluid dispenser having a chamber for storing a supply of fluid and a plunger reciprocally moveable within the chamber for dispensing the fluid, and a trigger operatively connected to the plunger and moveable to cause corresponding movement of the plunger. The apparatus also includes a generally elongated member connected to the handle member and an inflatable member supported at the distal end portion of the elongated member in fluid communication with the fluid dispenser. A method for performing a tracheostomy with the apparatus is also disclosed.

18 Claims, 18 Drawing Sheets

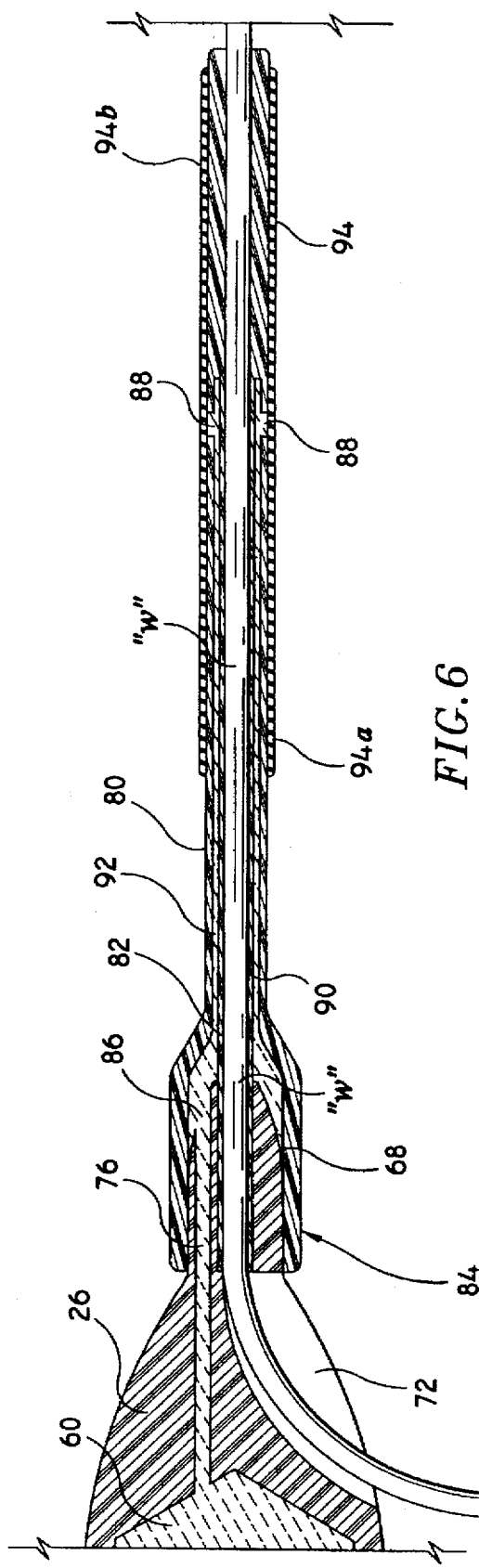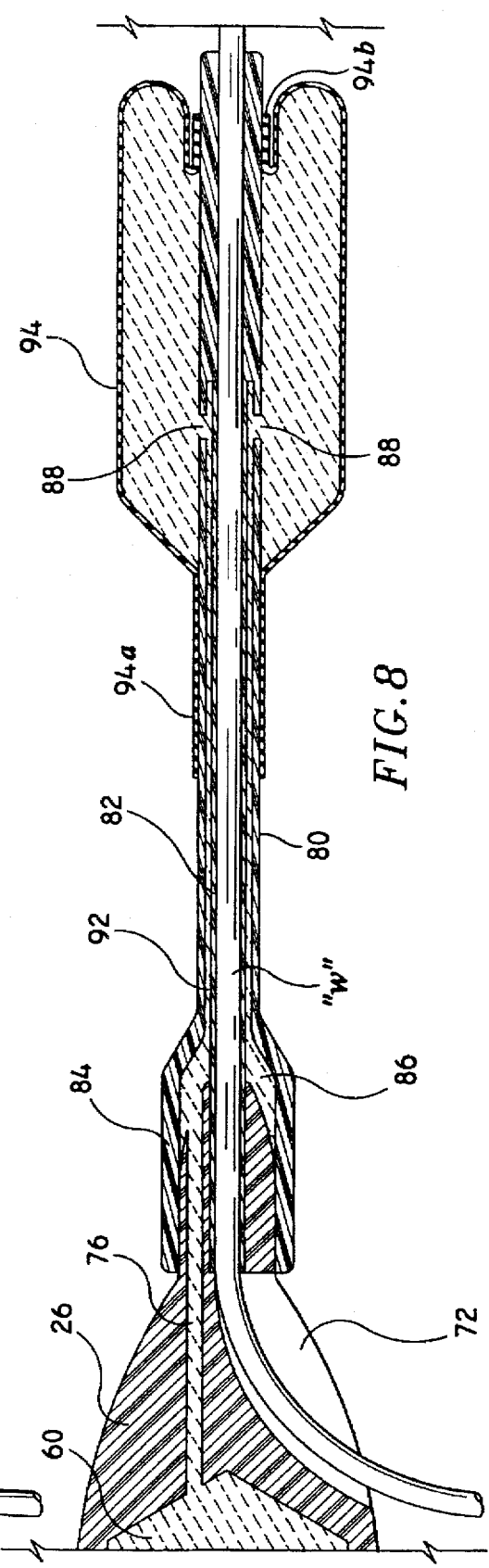

APPARATUS FOR EXPANDING BODY TISSUE

BACKGROUND

1. Field of the Disclosure

The present disclosure relates to an apparatus for expanding body tissue and, more particularly, to an apparatus incorporating an inflatable member which is selectively inflatable with a trigger mechanism. The present disclosure further relates to the surgical use of the apparatus in performing a tracheostomy.

2. Background of the Related Art

Surgical instruments incorporating inflatable membranes or balloons, commonly referred to as balloon catheter instruments, have a wide variety of applications including, for example, in angioplasty devices for clearing an occluded or blocked artery, in urethral sphincters, in tissue expanders or dilators, etc. . . . One type of balloon catheter incorporates a plunger disposed within a syringe housing. The plunger is axially advancable within the syringe housing in response to pressure directly applied to the rear end of the plunger to dispense the inflation fluid within the balloon. Another type of balloon catheter includes a plunger which is rotatably mounted within the syringe housing. The plunger distally translates in response to rotation thereof to dispense the inflation fluid into the balloon. Examples of conventional balloon catheters are described in U.S. Pat. Nos. 4,832,692; 5,084,060; 5,147,300; and 5,284,480.

Although conventional balloon catheters such as those described above and disclosed in the aforementioned patents have proven to be generally effective in certain applications, these devices suffer from a number of disadvantages which detract from their usefulness. In particular, one disadvantage of conventional balloon catheters is that such devices require a two handed operation, i.e., one hand creates the force necessary to move the plunger within the syringe housing while the other hand is used to hold and stabilize the catheter. As a consequence, the surgeon is incapable of performing any other surgical procedure during the application of the catheter. Other disadvantages of conventional balloon catheters include the inability to incrementally and selectively control the amount of fluid pressure supplied to the inflatable member, the insufficiency in providing structure to rapidly inflate or deflate the inflatable member and the relative complexity of the operating components.

U.S. Pat. No. 5,147,300 to Robinson et al. describes a balloon catheter instrument which attempts to address the aforementioned shortcomings of conventional instruments. The Robinson '300 instrument includes a housing, a syringe body and a handle. A threaded plunger is attached to the handle and advances within the syringe body in response to rotation of the handle. The instrument further includes a half nut mechanism which is selectively engagable with the threaded plunger. When the half nut mechanism is in engaged relation with the threaded plunger, the plunger is advanced by rotation of the handle. In the disengaged position of the half nut mechanism, the plunger may be advanced by depressing on the handle without any rotational movement.

There are certain disadvantages inherent in the design of the Robinson '300 instrument. For example, similar to the afore described balloon catheter devices, the Robinson '300 instrument requires a two handed operation—one hand to hold the instrument and the other hand to rotate the handle to advance the plunger. The half nut mechanism, although providing a means for rapidly inflating or deflating the balloon, is relatively complex thereby increasing cost of the instrument and decreasing the economic feasibility of disposing the instrument after a minimal number of uses.

Accordingly, the present disclosure is directed to an improved apparatus which is useful in performing a wide variety of surgical procedures such as angioplasty, tissue retraction, or tissue manipulation, etc. . . . The apparatus can be operated and manipulated with the single hand of the surgeon, thus, freeing the other hand to perform additional surgical functions. The apparatus includes structure to permit rapid inflation or deflation of an inflatable member supported at the distal end of the instrument. In addition, the apparatus is simple in design and relatively inexpensive to manufacture, thereby rendering the apparatus disposable after a minimal number of uses.

SUMMARY

Generally stated, the present disclosure is directed to a surgical apparatus for manipulating body tissue. The apparatus includes a handle member consisting of a frame, a self contained fluid dispenser having a chamber with a supply of inflation fluid and a plunger reciprocally moveable within the chamber for dispensing the inflation fluid, and a trigger operatively connected to the plunger and moveable to cause corresponding movement of the plunger. The apparatus further includes a generally elongated member connected to the handle member and an inflatable member supported at the distal end portion of the elongated member in fluid communication with the fluid dispenser. The elongated member may also include a longitudinal passageway for permitting passage of a guide wire used in positioning the apparatus in the body tissue.

In one preferred embodiment, the elongated member includes an outer tube and an inner tube coaxially mounted within the outer tube. The inner and outer tubes define a space therebetween which serves as an inflation lumen for supplying inflation fluid to the inflatable member. The outer tube may include at least one inflation aperture extending through an outer wall thereof in communication with the inflation lumen to permit passage of the inflation fluid into the inflatable member. The inner tube includes a longitudinal bore extending therethrough which defines the longitudinal passageway for reception and passage of the guide wire. In another preferred embodiment, the elongated member has an inflation lumen defined therein to permit inflation fluid to pass to the inflatable member.

The apparatus also includes a drive member which is connected at one end to the trigger and at another end to the plunger of the fluid dispenser. The drive member moves in response to movement of the trigger to cause corresponding reciprocal movement of the plunger within the chamber. The drive member is at least partially accommodated within a guide channel defined in the frame and is reciprocally axially movable therewithin. Preferably, the drive member is contiguously formed with the trigger and defines a generally arcuate configuration. A spring member may be provided to bias the trigger to an unactuated position.

The present invention is also directed to a method for performing a tracheostomy with the apparatus of the present disclosure. The method includes the steps of forming an opening in the trachea wall to gain access to the trachea, inserting a surgical apparatus having an inflatable member at least partially within the opening, inflating the inflatable member of the apparatus such that the inflatable member engages the trachea wall portions defining the opening thereby enlarging the opening, removing the surgical apparatus from the opening in the trachea wall and inserting a tracheostomy tube into the enlarged opening.

BRIEF DESCRIPTION OF THE DRAWINGS

Preferred embodiment(s) of the disclosure are described hereinbelow with reference to the drawings wherein:

FIG. 6 is an enlarged cross-sectional view of the elongated member apparatus illustrating the inflatable member in a deflated condition and the guide wire disposed within a longitudinal bore of the elongated member;

FIG. 8 is a view similar to the view of FIG. 6 illustrating the inflatable member in an expanded condition;

DETAILED DESCRIPTION OF THE PREFERRED EMBODIMENT(S)

The present invention is contemplated for use in surgical procedures where manipulation, retraction and/or dilation of a body structure is required. While the apparatus is particularly useful in performing a tracheostomy and will be described in connection with performing this procedure, it is to be appreciated that the apparatus has application to other surgical procedures as well. For example, the apparatus may be effectively used in enlarging or clearing an obstruction from vessels such as the coronary artery, fallopian tubes and urethral passages.

Figure 1:
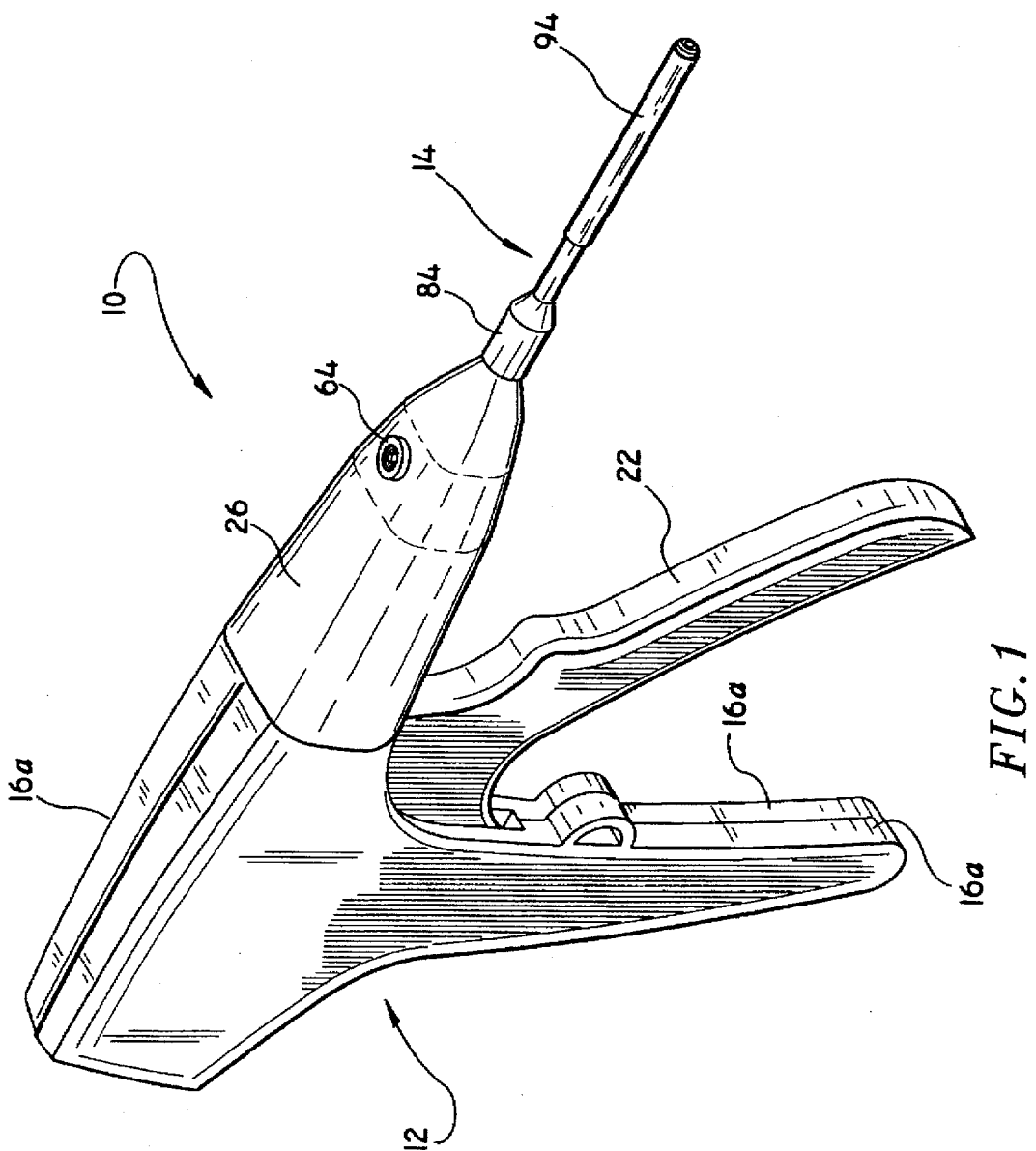
FIG. 1 is a perspective view of the apparatus in accordance with the principles of the present disclosure.
Figure 2:
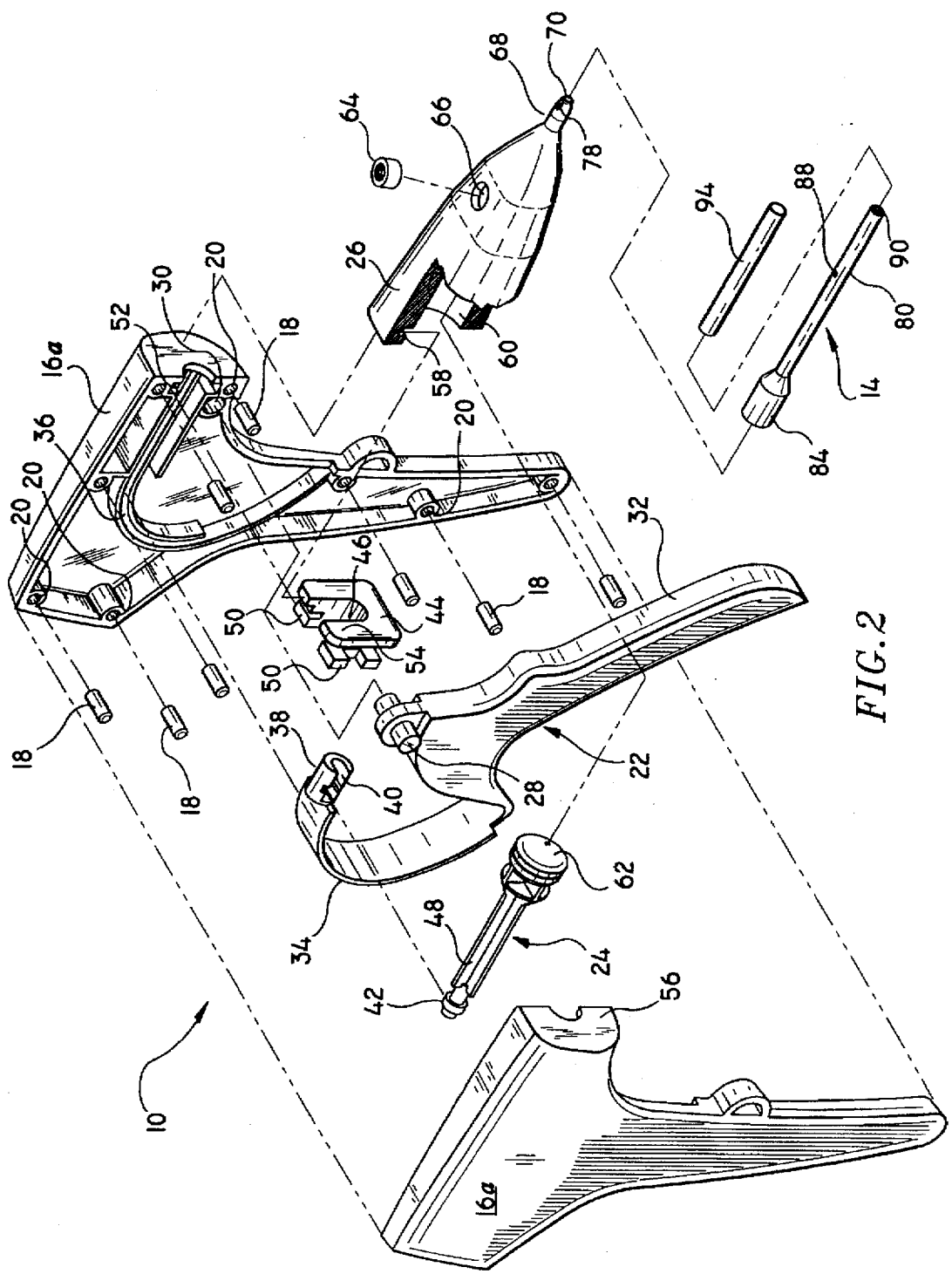
FIG. 2 is a perspective view with parts separated of the apparatus of FIG. 1, illustrating the handle unit and the elongated portion with the inflatable member.

Referring now to FIGS. 1–2, there is illustrated a preferred embodiment of the apparatus constructed in accordance with the principles of the present disclosure. Apparatus 10 includes handle unit 12 and elongated member 14 extending distally from the handle unit 12. Handle unit 12 includes frame or housing 16 consisting of two half sections 16a affixed to each other. In a preferred mounting method shown in FIG. 2, a plurality of mounting pins 18 are received within respective mounting apertures 20 defined in half sections 16a to assist in mounting the half sections 16a. Mounting pins 18 may be secured within mounting apertures 20 with cements, adhesives, or the like. Other means for affixing half sections 16a to each other may be readily determined by one skilled in the art such as with the use of adhesives, screws or other conventional means.

Handle unit 12 further includes trigger 22, plunger 24 and nose hub 26. Trigger 22 is pivotally mounted to housing 16 about pivot pin 28. Pivot pin 28 is preferably contiguously formed with trigger 22 as shown in FIG. 2 and is received within trigger mounting apertures 30 formed in each half section 16a to effectuate the mounting. Trigger 22 includes grip portion 32 having a contoured gripping surface strategically dimensioned to be grasped by the user. A drive portion 34 extends from grip portion 32 and is contiguously formed therewith. Drive portion 34 follows an arcuate path and is received within correspondingly dimensioned arcuate guide channels 36 formed in each half section 16a. Drive portion 34 traverses guide channels 36 in response to pivoting movement of trigger 22.

Figure 3:
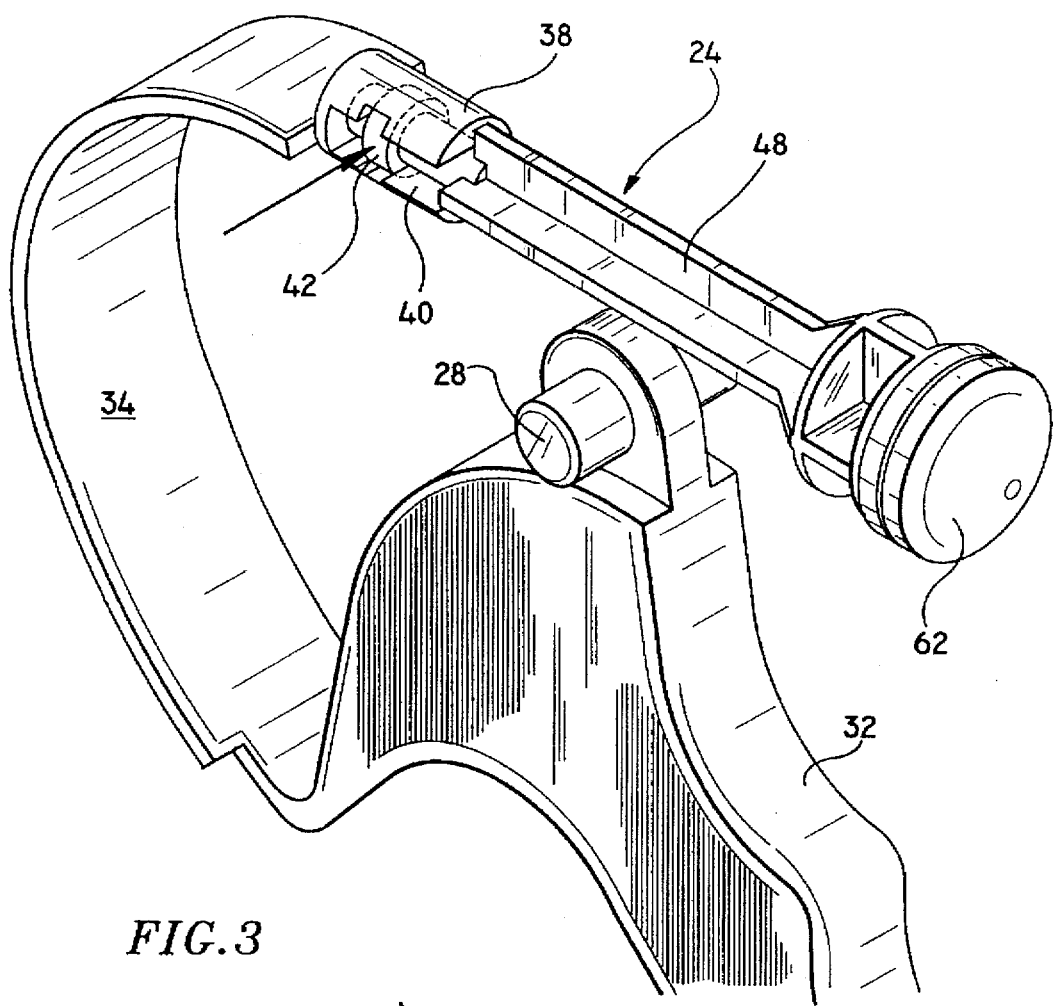
FIG. 3 is a perspective view of the trigger, drive member and plunger of the handle assembly.

Referring now to FIGS. 2–3, drive portion 34 extending from trigger 22 is operatively connected to plunger 24 by connecting member 38 which extends outwardly from the drive portion 34. Connecting member 38 defines a generally cylindrical cross-section and has a grooved or recessed portion 40 formed in its outer wall surface. Recessed portion 40 receives a correspondingly dimensioned mounting portion 42 defined at the proximal end of plunger 24 to effectuate the mounting of drive portion 34 to the plunger 24. In a preferred mounting method, mounting portion 42 of plunger 24 snaps into recessed portion 40 of connecting member 38 in the direction indicated by the directional arrow of FIG. 3 to fixedly secure the two components to each other. Other means for connecting drive portion 34 to plunger 24 may be readily envisioned by one skilled in the art.

Figure 4:
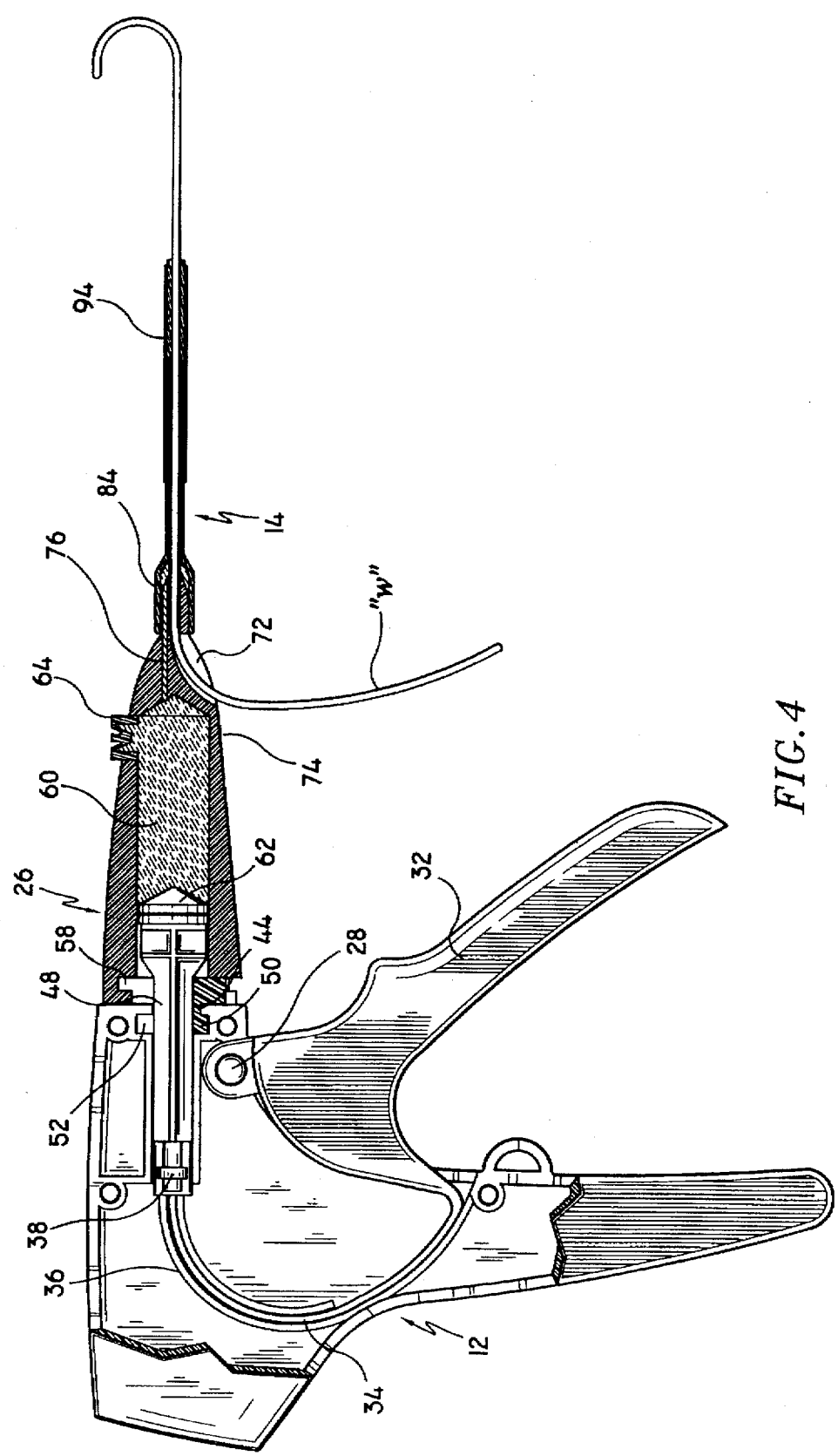
FIG. 4 is a side plan view in partial cross-section of the apparatus of FIG. 1 in an unactuated position.

Referring now to FIG. 2, in conjunction with FIG. 4, handle unit 12 also includes nose hub mount 44. Nose hub mount 44 defines a centrally-disposed semi-circular recess 46 which accommodates elongated portion 48 of plunger 24 and two pairs of opposed laterally extending mounting projections 50. Mounting projections 50 each possess a generally rectangular cross-section and are received within correspondingly dimensioned rectangular recesses 52 formed in half sections 16a to mount nose hub mount 44 to the half sections 16a. Nose hub mount 44 also includes opposed vertically extending projections 54 adjacent semi-circular recess 46. Laterally extending projections 54 serve in mounting nose hub 26 to housing 16 as will be appreciated from the description provided hereinbelow.

Referring now to FIGS. 1, 2 and 4, nose hub 26 is mounted to the distal end face 56 of housing 16. At its proximal end, nose hub 26 includes a generally rectangular-shaped groove 58 in an upper interior surface thereof.

Groove 58 accommodates both vertically extending projections 54 (FIG. 2) of nose hub mount 44 to mount nose hub 26 to housing 14. It is envisioned that nose hub 26 may also be affixed to distal end face 56 with suitable means including adhesives, cements, etc. . . . Nose hub 26 has an interior chamber or plunger housing 60 formed therein which stores the inflation fluids disposed by plunger 24. Chamber 60 is generally circular in cross-section to correspond to the generally circular plunger head 62 of plunger 24. A pressure indicator 64 is in communication with chamber 60 and sits within a correspondingly dimensioned opening 66 in the upper surface of nose hub 26. Pressure indicator 64 indicates to the user when the pressure within chamber 60 exceeds a predetermined value, e.g., 100 psi.

Figure 5:
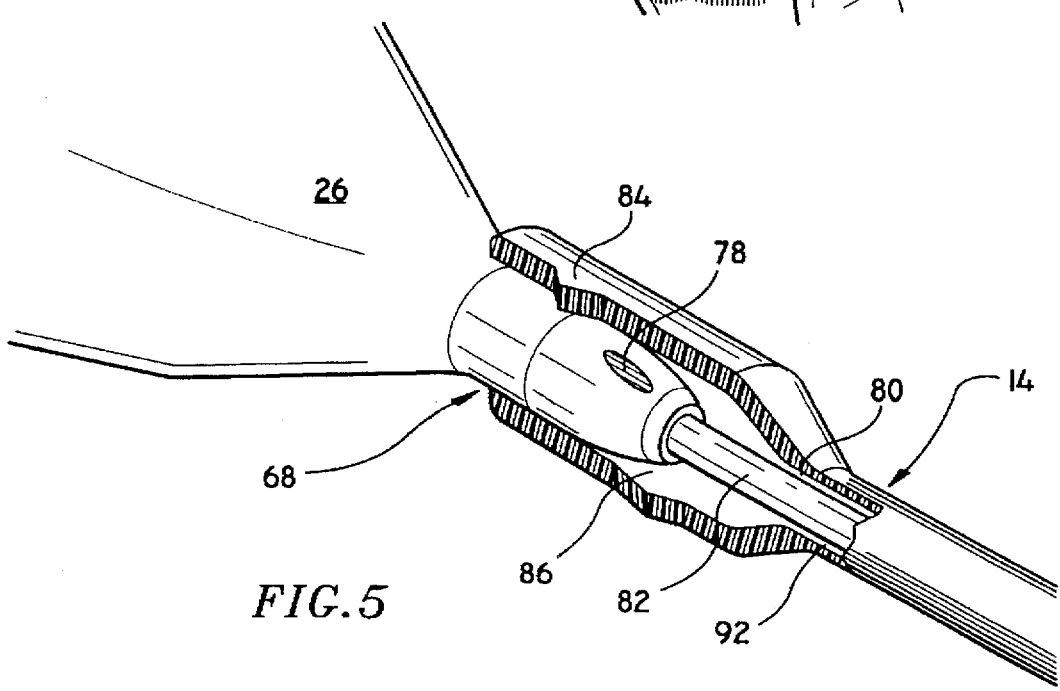
FIG. 5 is a perspective view with portions cut-away of the distal end of the nose hub of the handle unit, illustrating mounting of the elongated member to the nose hub.

Referring to FIGS. 2, 4 and 5, nose hub 26 distally terminates in a hub distal portion 68. Hub distal portion 68 defines a narrow configuration and has a centrally disposed aperture 70 (FIG. 2) formed therein. Hub distal portion 68 also includes an arcuate guide channel 72 (FIG. 4) which is in communication with aperture 70 and extends through a lower surface 74 of nose hub 26. Aperture 70 and guide channel 72 accommodate a guide wire "w" and permit passage of the guide wire "w" during use of apparatus 10. Nose hub 26 further includes an inflation channel 76 (FIG. 4) which permits passage of the inflation fluids dispensed by plunger 24 within chamber 60. Inflation channel 76 is in communication at one end with chamber 60 and extends through hub distal portion 68 where it terminates in generally elliptically-shaped inflation aperture 78 formed in the outer surface of the hub distal portion 68 as best shown in FIGS. 2 and 5.

The above-described elements including housing 14, trigger 22, plunger 24 and nose hub 26 defining plunger housing or chamber 60 constitute the handle or frame unit 12 of apparatus 10. The components of handle unit 12 are preferably fabricated from polymeric materials and are formed by known injection molding techniques. It is also envisioned that the components of handle unit 12 may be fabricated from metallic materials including stainless steel, aluminum alloy or the like.

Referring now to FIG. 6, in conjunction with FIGS. 2 and 4, elongated member 14 includes an outer tube 80 and an inner tube 82 coaxially mounted within the outer tube 82. The proximal end portion of outer tube 80 includes mounting hub 84. Mounting hub 84 defines a generally circular longitudinal bore 86 which accommodates hub distal portion 68 to mount elongated member 14 to housing 16. Preferably, longitudinal bore 86 and hub distal portion 66 are correspondingly dimensioned such that a friction fit is formed between the two components. Mounting hub 84 may also be adhered to hub distal portion 68 to fixedly secure the two components. Outer tube 80 also includes two inflation apertures 88 in its exterior wall, the function of which will be appreciated from the description provided hereinbelow.

Inner tube 82 of elongated member 14 defines axial bore 90 (FIG. 2) extending therethrough. Axial bore 90 accommodates guide wire "w" during use of the apparatus. In particular, guide wire "w" is inserted into axial bore 90 and passed through the bore 90 and out channel 72 of nose hub 26.

The coaxial mounting of inner tube 82 within outer tube 80 defines an annular space 92 (FIGS. 5 and 6) between the two tubes 80, 82. Annular space 92 is dimensioned to define an enclosed fluid passageway to pass the inflation fluids exiting inflation channel 76 of nose hub 26 to the distal end portion of elongated member 14 where the fluids exit through the two inflation apertures 88.

Referring still to FIGS. 2, 4, and 6, an inflatable member or balloon 94 is coaxially mounted about the distal end portion of outer tube 80. Inflatable member 94 is preferably fabricated from a resilient material preferably polyethylene terephthalate (PET). PET material provides inflatable member 94 with very low expansion characteristics such that the balloon in its pre-assembled or non-inflated state has substantially the equivalent dimensions as the balloon in its fully inflated state. An inflatable member 94 fabricated from PET also becomes very hard when inflated, which is desirable in certain applications, particularly, when performing a tracheostomy as will be discussed. A suitable balloon or inflatable member 94 for this purpose is manufactured by Advanced Polymers, Inc. of Salem, Mass.

Figure 6A:
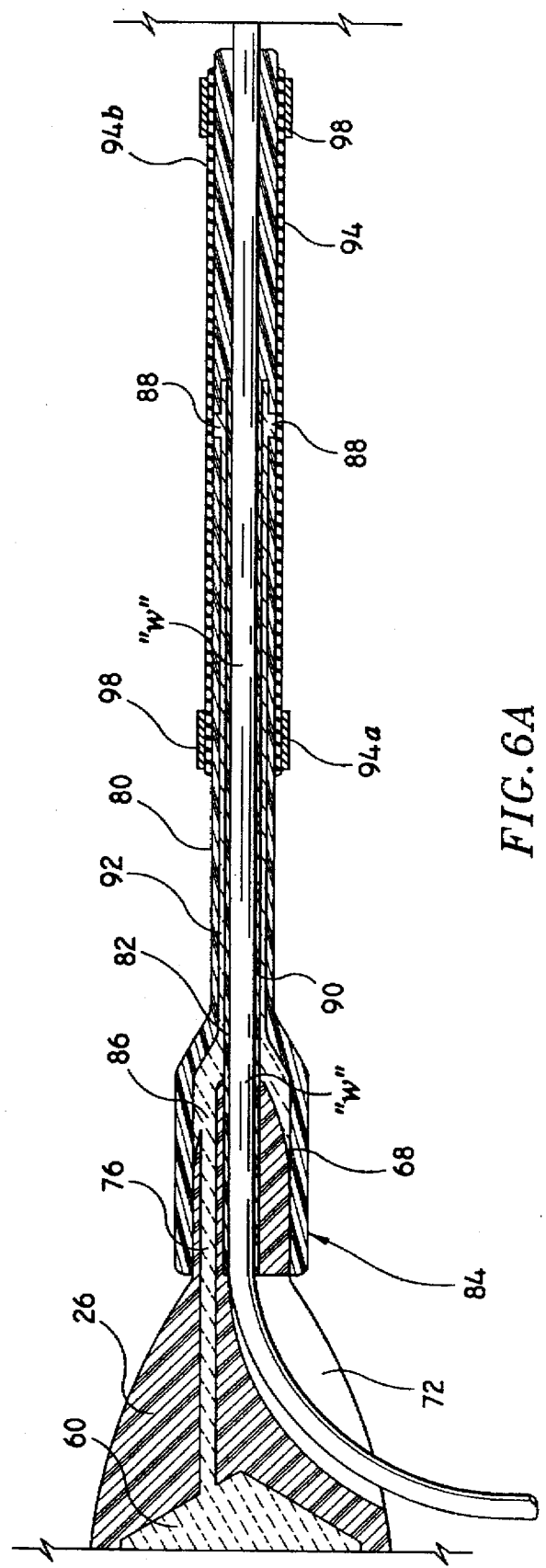
FIG. 6A is a view similar to the view of FIG. 6 illustrating the use of balloon mounting rings to mount the inflatable member to the elongated member.

Inflatable member 94 inflates upon passage of the inflation fluids through inflation apertures 88 of outer tube 80. Inflatable member 94 preferably forms a fluid tight seal at its end portions 94a, 94b (FIG. 6) to prevent leakage of the inflation fluids dispensed by plunger 24. In a preferred mounting method, inflatable member 94 defines a longitudinal bore 96 which has a dimension or cross-section which approximates the cross-sectional dimension defined by elongated member 14 to form a slip fit between the end portions 94a, 94b and the elongated member 14. End portions 94a, 94b may be adhered to elongated member 14 to further secure in fluid tight manner the inflatable member 94 to the elongated member 14. In the alternative, balloon mounting rings or sleeves 98 may be used to mount inflatable member 94 to elongated member 14 as depicted in FIG. 6A. Mounting sleeves 98 are appropriately dimensioned to fit over end portions 94a, 94b of inflatable member 94 and circumferentially compressed (by conventional means including crimping dies, etc. . . . ) thereby effecting a seal of the inflatable member 94 to the elongated member 14. Pressure held by this technique exceeds 300 psi.

OPERATION OF THE APPARATUS

The operation of apparatus 10 will now be discussed. Referring initially to FIGS. 4 and 6, when it is desired to manipulate or dilate tissue during a surgical procedure, the surgeon grasps handle unit 12 and positions the apparatus 10 adjacent the tissue to be expanded. In accordance with a preferred method of using apparatus 10, guide wire "w" is employed to facilitate the positioning of inflatable member 94 within the tissue to be manipulated. In particular, guide wire "w" is positioned within the tissue so as to assist in guiding the apparatus 10 into the tissue structure. Once guide wire "w" is in place, the proximal end of guide wire "w" is fed through longitudinal bore 90 of inner tube 82 (FIG. 2) via the distal opening of the bore and advanced until it passes through aperture 70 (FIG. 2) of nose hub 26 and arcuate guide channel 72 where it extends out the guide channel 72 (FIGS. 4 and 6). Apparatus 10 is then advanced along guide wire "w" until inflatable member 94 is adjacent the targeted tissue.

Figure 7:
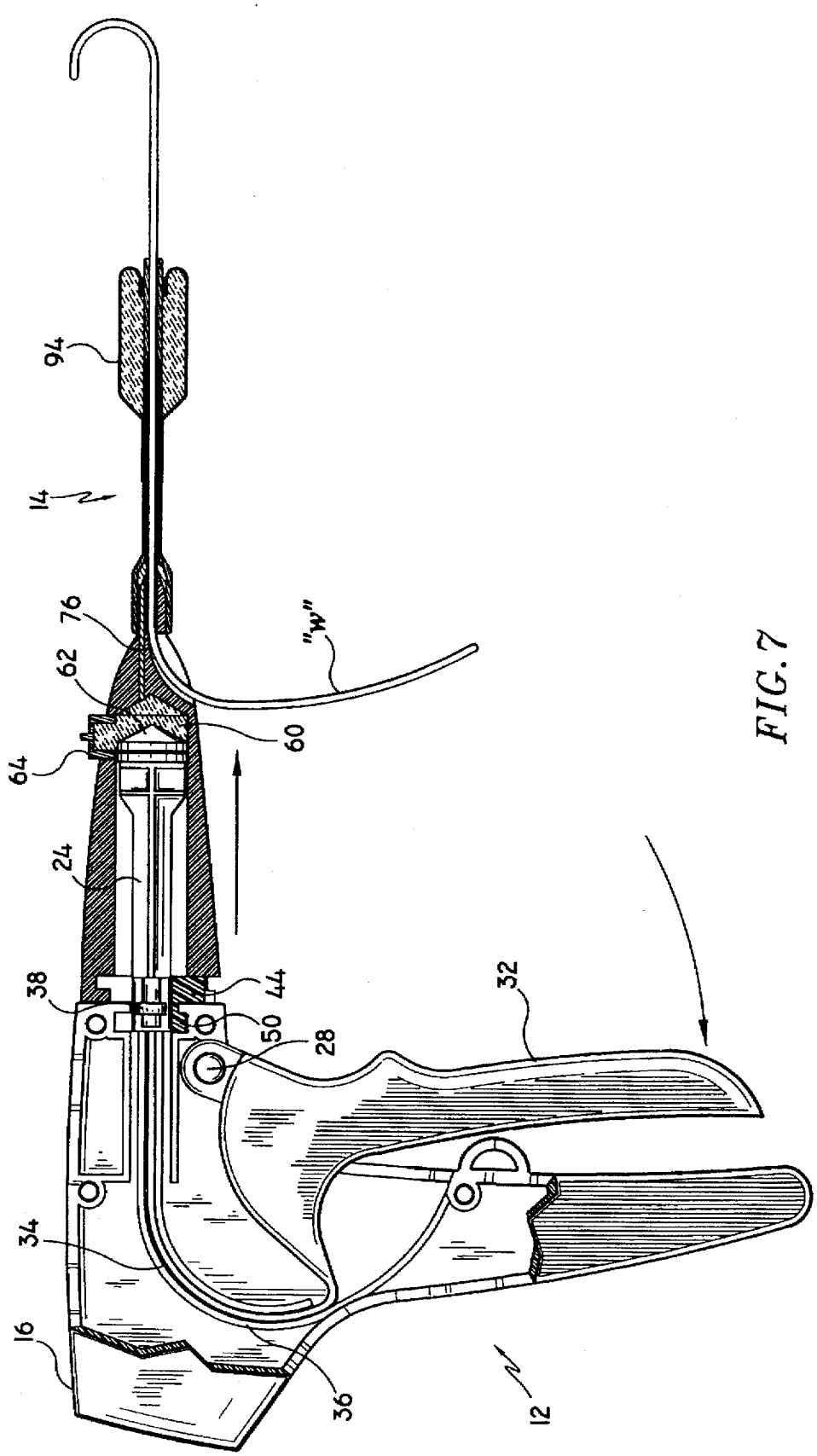
FIG. 7 is a view similar to the view of FIG. 4 illustrating the apparatus in an actuated position with the trigger depressed to inflate the inflatable member.

The surgeon then grasps grip portion 32 of trigger 22 with his fingers and selectively depresses the grip portion 32 in a proximal direction as shown by the directional arrow of FIG. 7. As trigger 22 pivots about pivot pin 28, drive portion 34 traverses arcuate guide channels 36 to distally translate plunger 24 within chamber 60 in the direction of the directional arrow of FIG. 7. Plunger 24 forces the inflation fluids out chamber 60 through inflation channel 76 of nose hub 26 where the fluids are dispensed through inflation aperture 78 of nose hub 26 (FIG. 5) and into the annular space 92 defined between outer and inner tubes 80, 82. The inflation fluids pass through annular space 92 and out the two opposed inflation apertures 88 formed in outer tube 80 to inflate inflatable member 94 as shown in FIGS. 6 and 8. Inflatable member 94 expands to engage and dilate the tissue.

Apparatus 10 of the present disclosure provides significant advantages over conventional balloon catheter systems. Handle 12 is operable with a single hand of the surgeon, thus, freeing the surgeon's other hand to perform other surgical functions. Due to the mechanical advantages provided through the trigger 22 and connected plunger 26, the force required on behalf of the surgeon to expand the inflatable member 94 is greatly minimized. Further, the concentric mounting of inflatable member 94 about elongated member 14 provides for uniform radial expansion of the inflatable member 94, therefore, resulting in uniform dilation of the tissue structure.

USE OF THE APPARATUS IN PERFORMING A TRACHEOSTOMY

Figure 9:
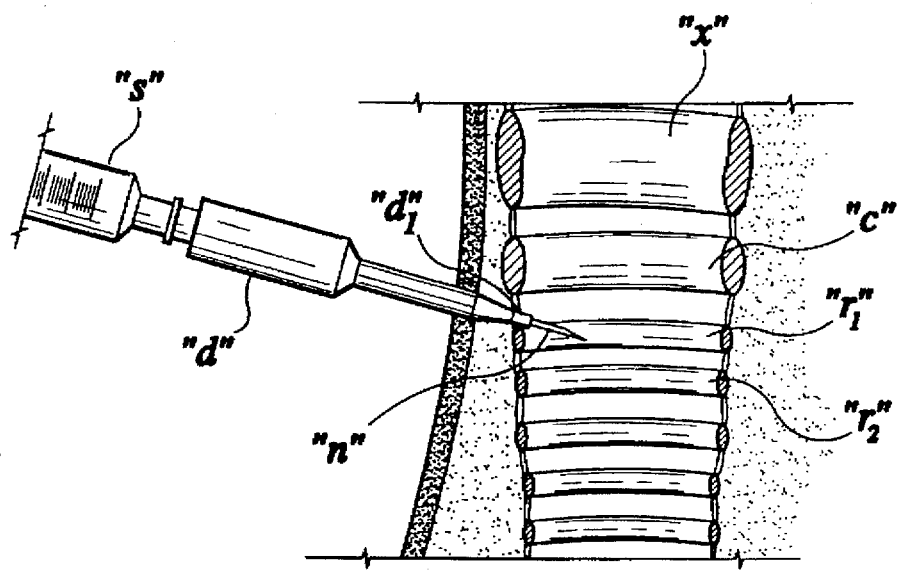
FIGS. 9–13 are views illustrating a preferred method for performing a tracheostomy with the apparatus of FIG. 1.
Figure 10:
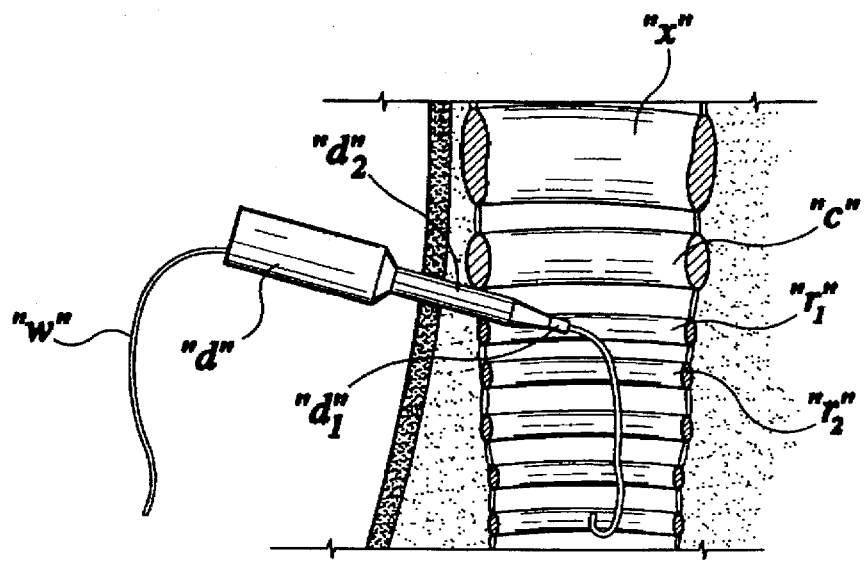

The use of apparatus 10 in conjunction with a novel method for performing a tracheostomy is best illustrated in FIGS. 9-13 where the trachea of a patient is shown. Referring initially to FIG. 9, local anesthesia is applied to the tracheal area and an incision is made at the desired location adjacent the cricoid cartilage "c". A dilator "d" is then positioned over the needle portion "n" of a syringe "s". The needle portion "n" having the dilator "d" positioned thereover is inserted within the trachea as shown in FIG. 9. In one preferred method, the needle portion "n" and the dilator "d" is directed to pass between the cricoid cartilage "c" and the first tracheal ring "$r_1$". In the alternative, the needle portion "n" and dilator "d" may be inserted between the first tracheal ring "$r_1$" and a second tracheal ring "$r_2$", or between the cricoid cartilage "c" and the thyroid cartilage "x". During the initial insertion step (shown in FIG. 9), dilator "d" is inserted a predetermined distance whereby only the first diameter portion "$d_1$" penetrates the trachea and engages the adjacent tracheal rings. With the needle portion "n" of the syringe "s" penetrating the trachea, the syringe "s" is used to dispense an anesthetic (e.g., lidocaine) into the tracheal lumen by depressing the plunger of the syringe "s". Thereafter, the plunger of the syringe "s" is withdrawn slowly. Upon withdrawal of the plunger, the presence of air bubbles in the syringe "s" indicates that the needle tip is appropriately placed in the tracheal lumen. The syringe "s" is then removed leaving dilator "d" in place within the adjacent tracheal rings. After the needle portion "n" is removed, the surgeon advances the dilator "d" within the tracheal area until its second larger diameter portion "$d_2$" engages the adjacent rings as shown in FIG. 10.

Referring still to FIG. 10, a guide wire "w" is positioned within a bore defined in dilator "d" and the guide wire "w" is advanced distally within the dilator "d" until a distal portion of the guide wire "w" is within the trachea of the patient. It is to be noted that the guide wire "w" may be inserted prior to advancing dilator "d" within the trachea to its second diameter portion "$d_2$". With guide wire "w" in place, dilator "d" is removed from the surgical site.

It is to be noted that the procedure could be performed without the use of dilator "d". In particular, needle portion "n" of syringe "s" could be used to penetrate the trachea. Thereafter, guide wire "w" could be advanced within a bore defined in needle portion "n" and positioned within the trachea site. In the alternative, needle portion "n" could be used to form the opening in the trachea and then removed followed by direct insertion of the guide wire "w" between the adjacent trachea rings.

Figure 11:
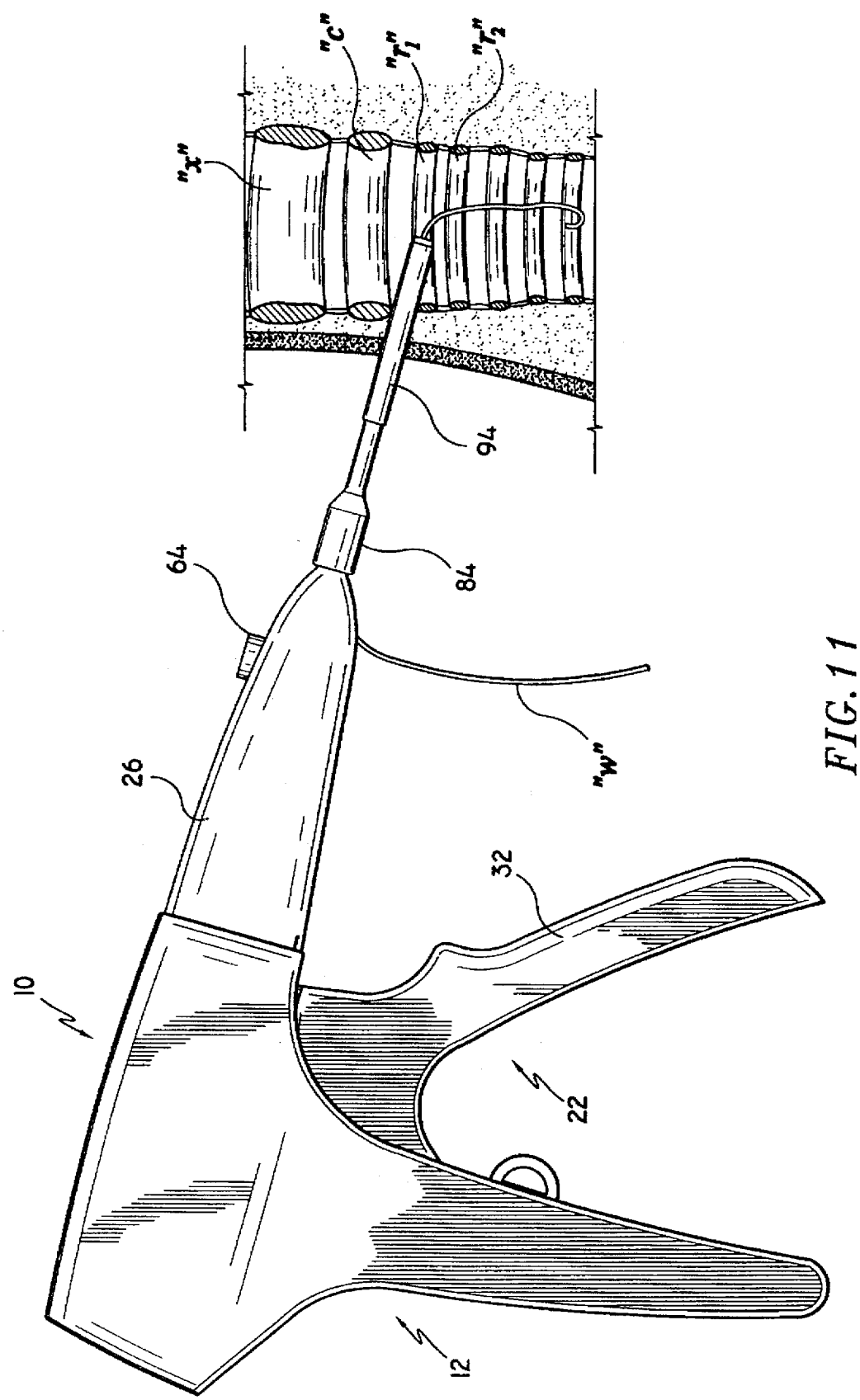
Figure 12:
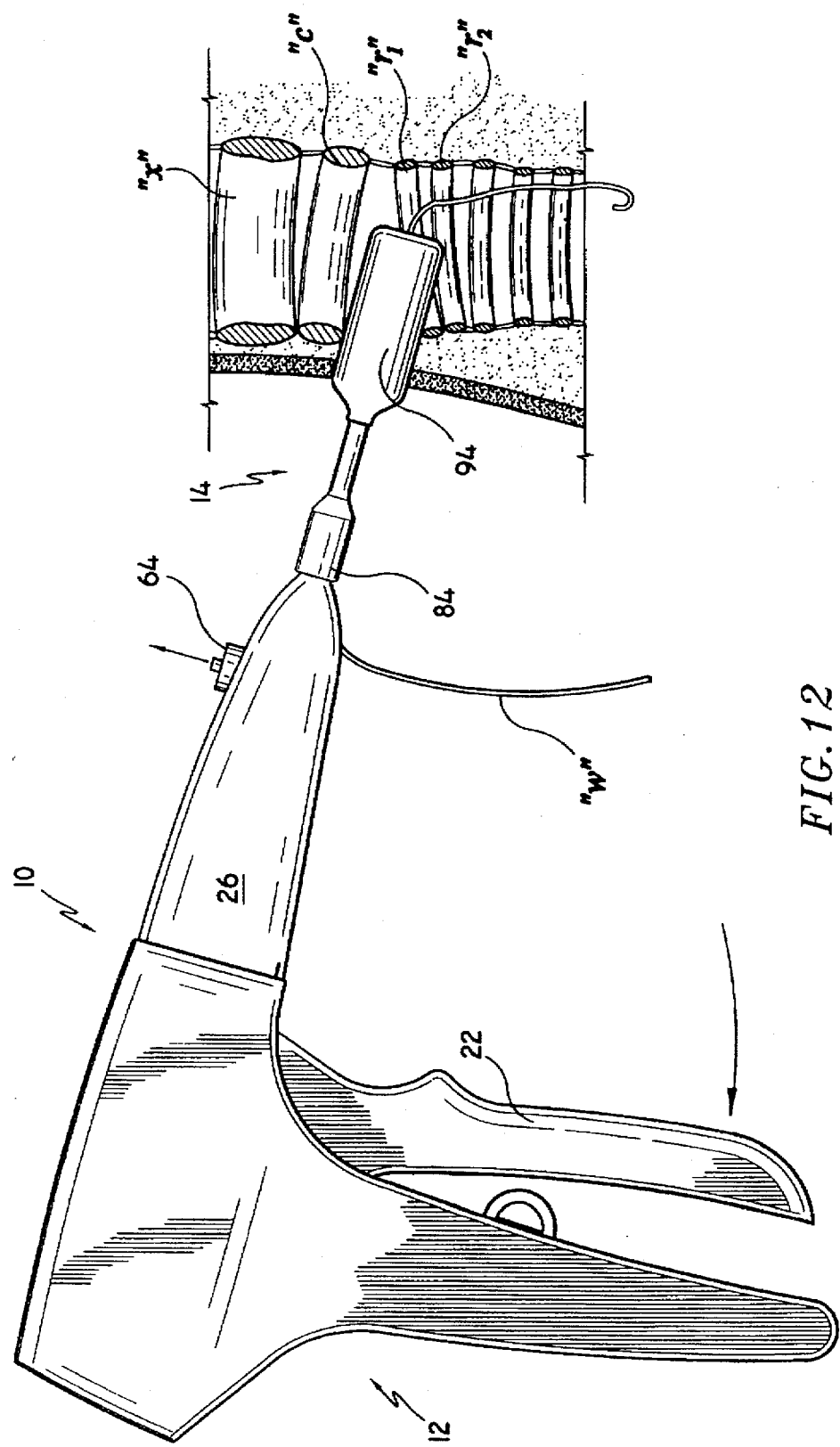

With guide wire "w" in place, the surgeon then directs his attention to applying apparatus 10 of the present disclosure. The proximal end portion of guide wire "w" is positioned within longitudinal bore 90 (FIG. 2) of inner tube 82 and the wire "w" is fed through the bore 90 and advanced through guide channel 72 of nose hub 26 as depicted in FIGS. 4 and 6. Referring now to FIG. 11, apparatus 10 is advanced along guide wire "w" until inflatable member 94 is positioned within the adjacent tracheal rings as shown. With reference to FIG. 12, the surgeon depresses trigger 22 in the direction indicated by the directional arrow to selectively inflate inflatable member 94. As inflatable member 94 inflates, the adjacent trachea rings are displaced from each other to define the enlarged space shown in FIG. 12. During the inflation of inflatable member 94, it is to be noted that if the pressure within chamber 60 exceeds the predetermined limit as set by pressure indicator 64, the indicator 64 would actuate to indicate to the user of the relatively high pressure.

Figure 13:
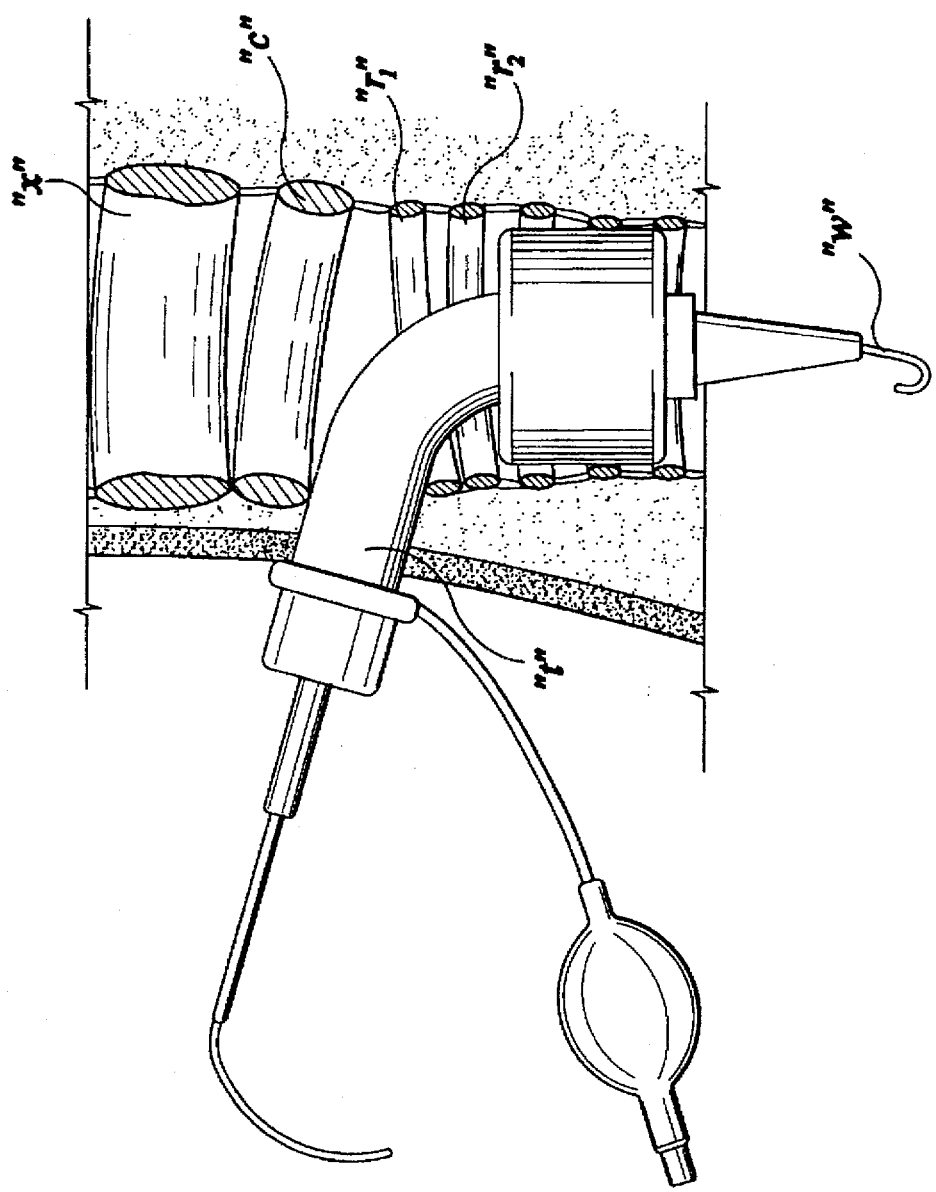

The procedure is continued by deflating inflatable member 94. This is accomplished by pivotally moving trigger 22 in a direction opposite to the directional arrow of FIG. 12. With inflatable member 94 deflated, the apparatus 10 is removed. Referring now to FIG. 13, a conventional tracheostomy tube "t" is positioned within the enlarged space defined between the adjacent tracheal rings as provided by the expansion of inflatable member 94. FIG. 13 illustrates the tracheostomy tube "t" appropriately positioned within the trachea.

Thus, in accordance with the novel method for performing a tracheostomy of the present disclosure, the inflatable member 94 is employed to provide an enlarged opening between the adjacent tracheal rings to permit insertion of a tracheostomy tube "t". The use of apparatus 10 with inflatable or balloon member 94 has significant advantages over conventional tracheostomy methods. In accordance with conventional methods for performing a tracheostomy, dilating tubes of varying increasing sizes are forcibly inserted into an opening in the trachea to gradually enlarge the opening. This often requires a significant amount of force on behalf of the surgeon to insert the dilating tubes. Furthermore, forcing the dilating tubes inwardly into the trachea increases the potential of damaging underlying tissue structure. However, with the apparatus 10 of the present disclosure, the inflatable member 94 of the apparatus is easily positioned within the initial opening. Thereafter, the inflatable member 94 is expanded to perform gradual uniform radial dilation and expansion of the adjacent tracheal rings. The force required is relatively low due to the mechanical advantages as provided through the handle unit 12.

Figure 14:
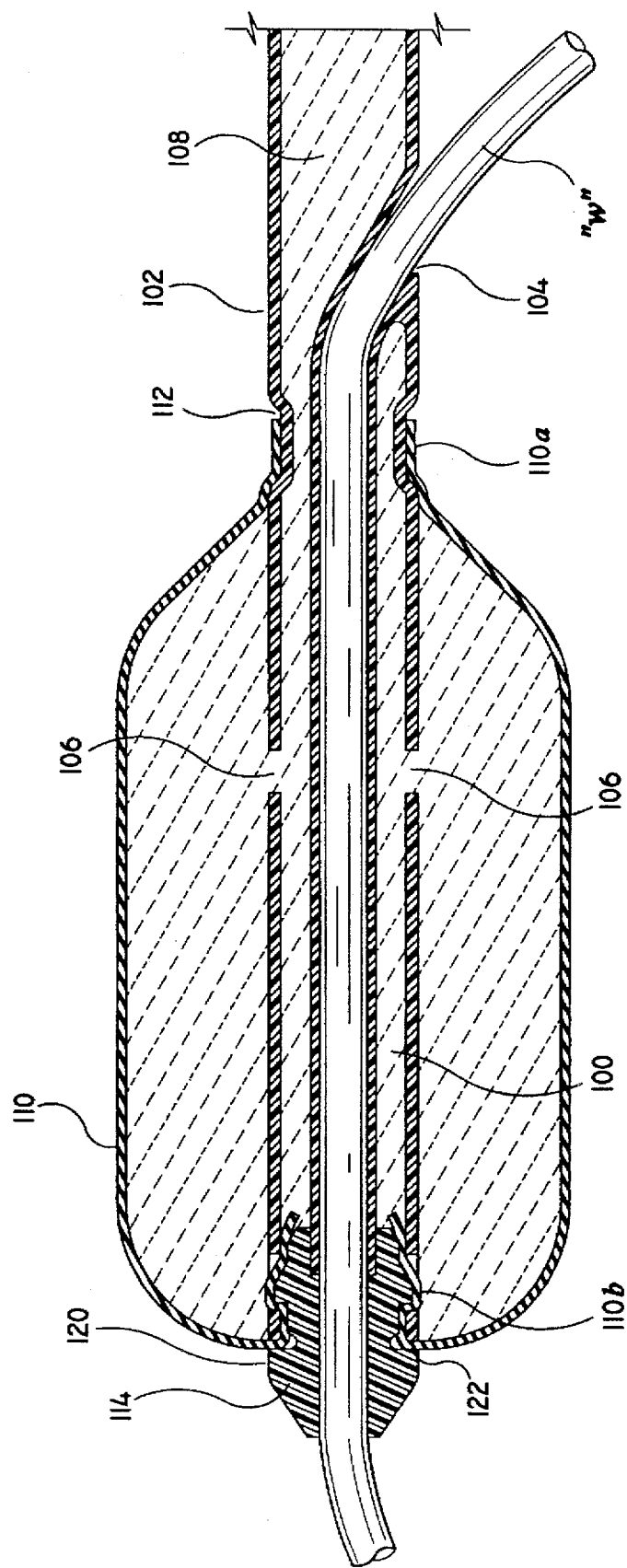
FIG. 14 is a cross-sectional view of the distal portion of the elongated member illustrating a preferred mechanism for securely mounting the inflatable member to the elongated member.
Figure 15:
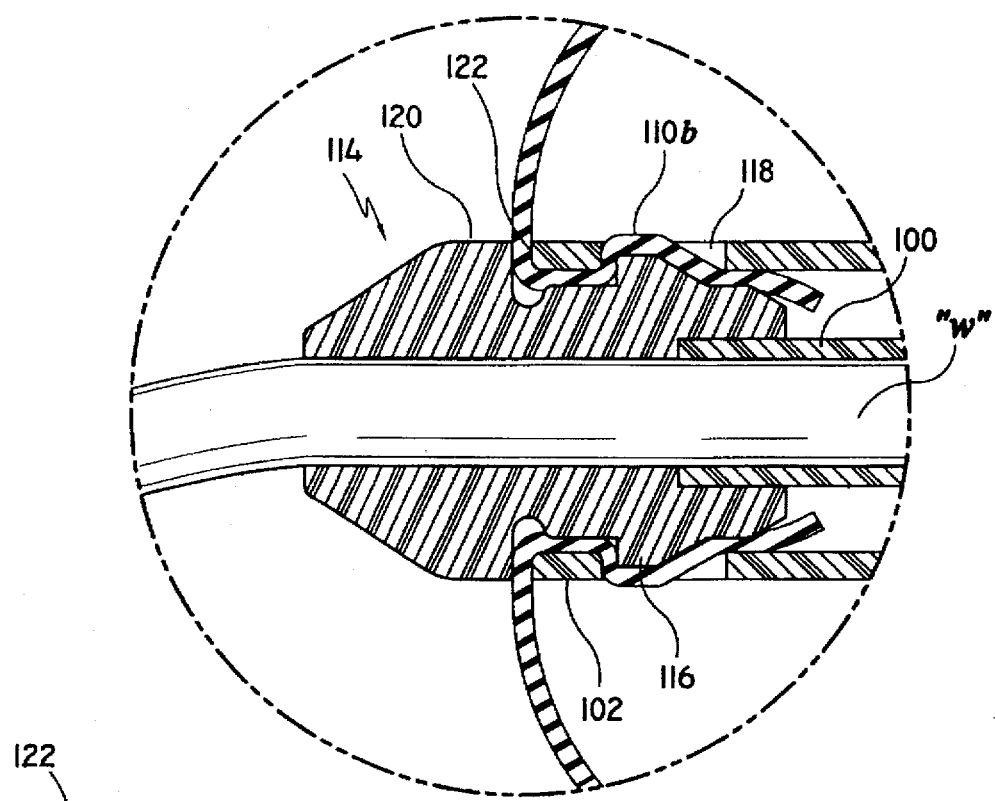
FIG. 15 is an enlarged isolated view of the mounting mechanism of FIG. 14.
Figure 16:
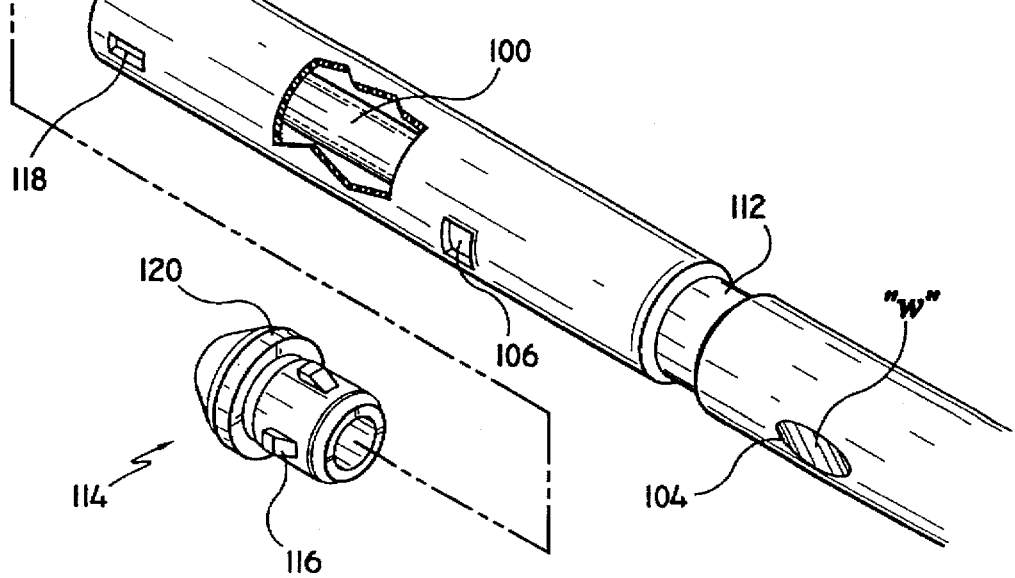
FIG. 16 is an enlarged perspective view with parts separated further illustrating the mounting mechanism of FIG. 14.
Figure 17:
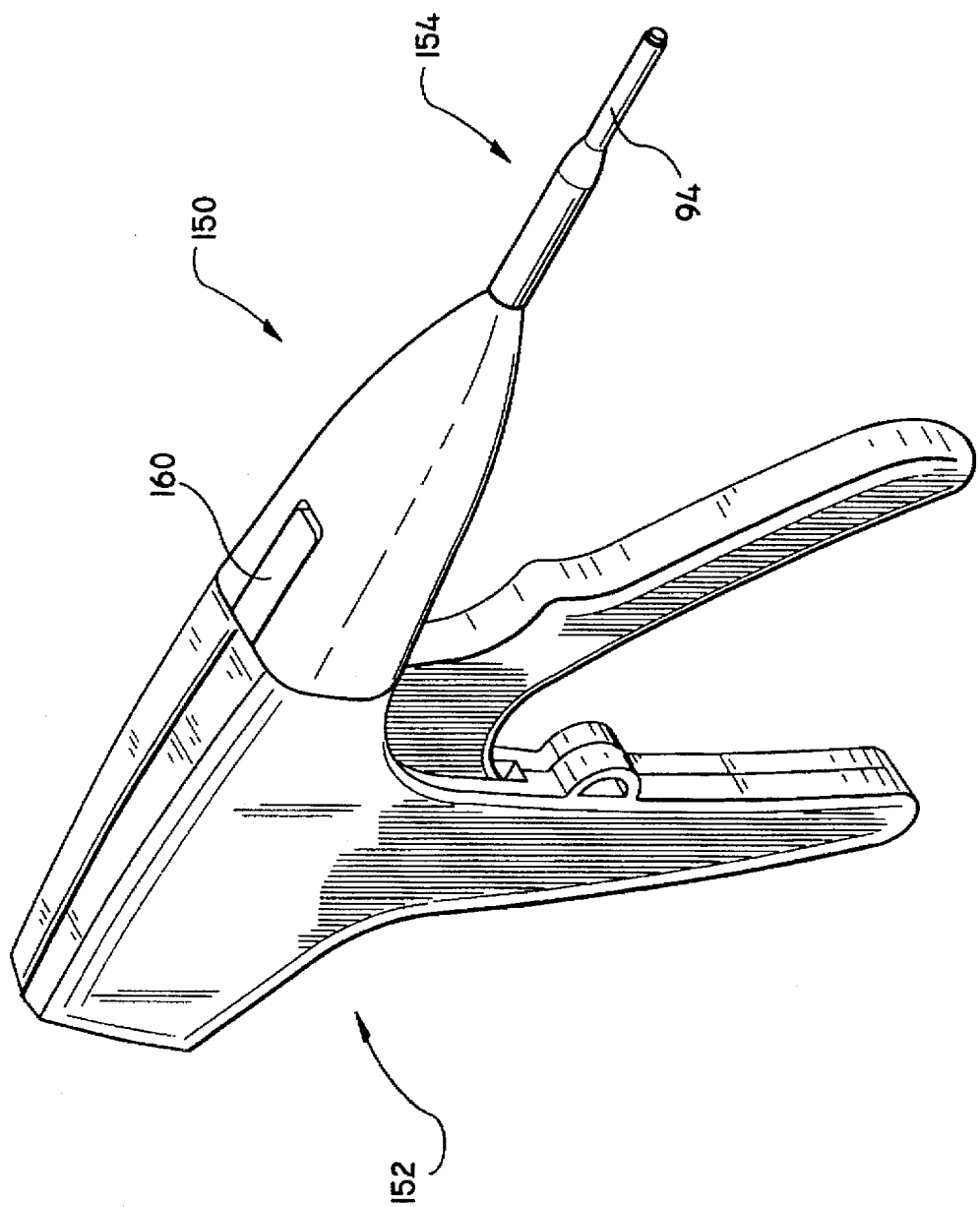
FIG. 17 is a perspective view of an alternate embodiment of the apparatus of FIG. 1.
Figure 18:
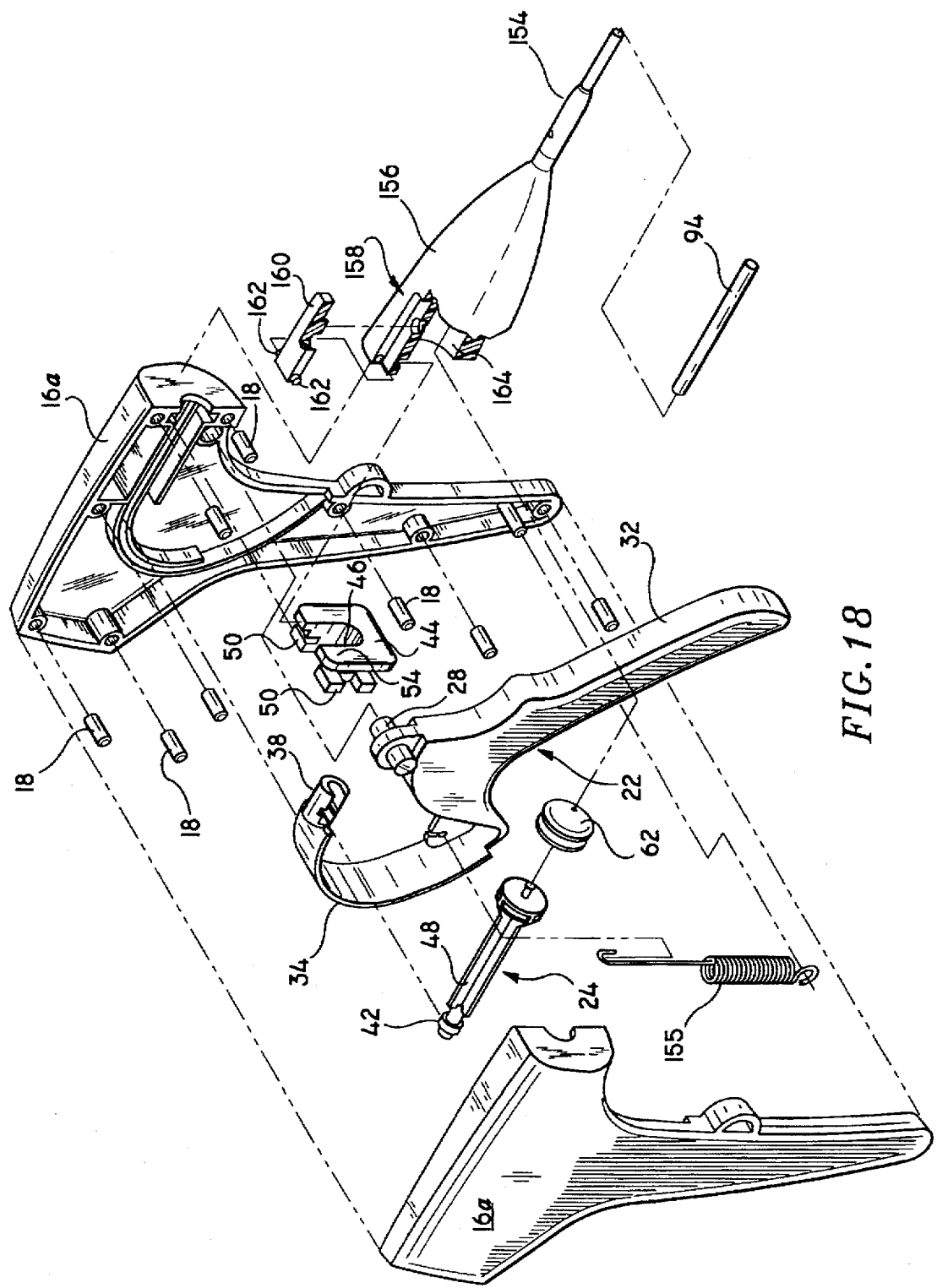
FIG. 18 is a perspective view with parts separated of the apparatus of FIG. 17.
Figure 19:
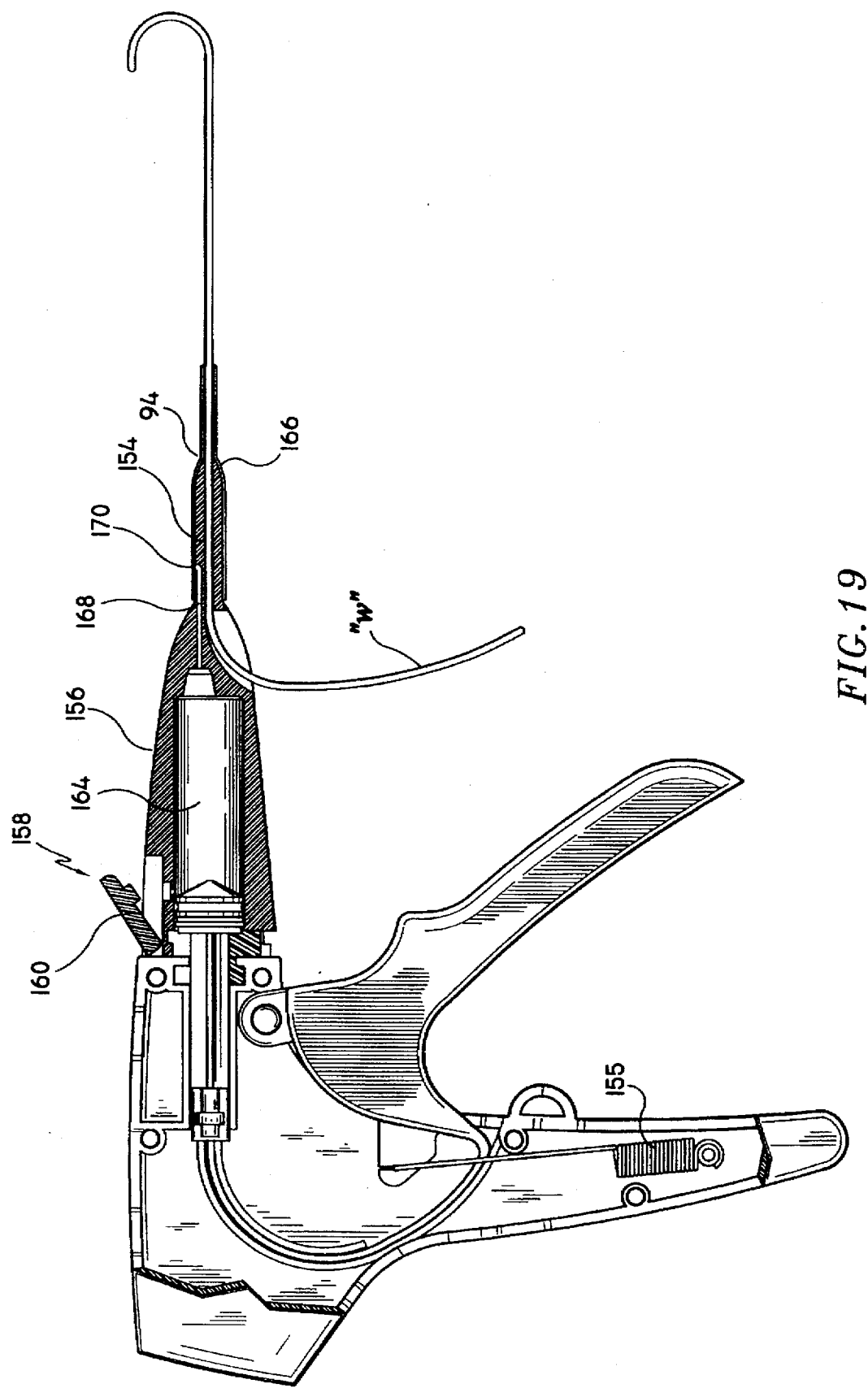
FIG. 19 is a side plan view in partial cross-section of the apparatus of FIG. 17 in an unactuated position.
Figure 20:
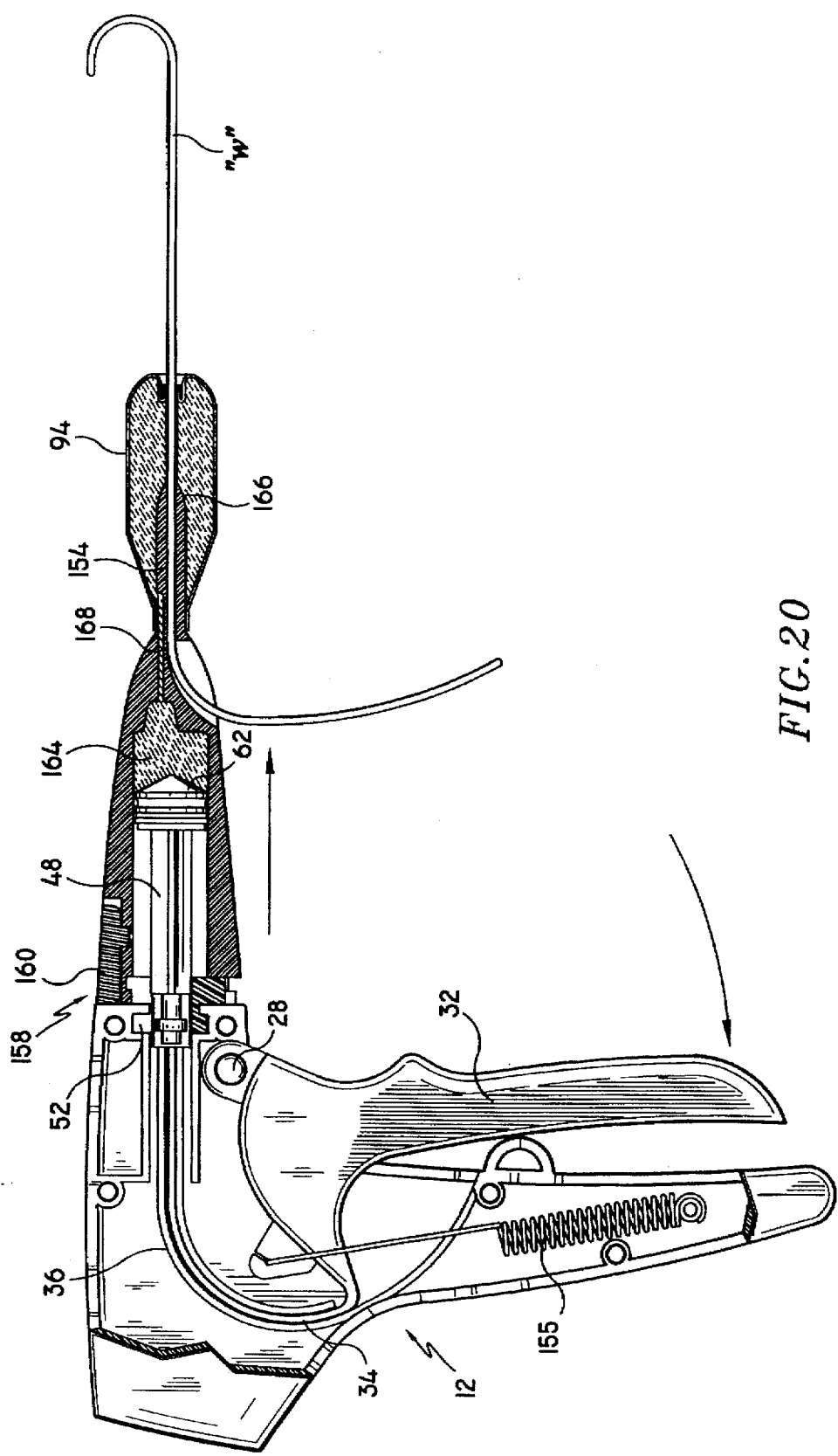
FIG. 20 is a view similar to the view of FIG. 19 illustrating the apparatus in an actuated position with the trigger depressed to inflate the inflatable member.
Figure 21:
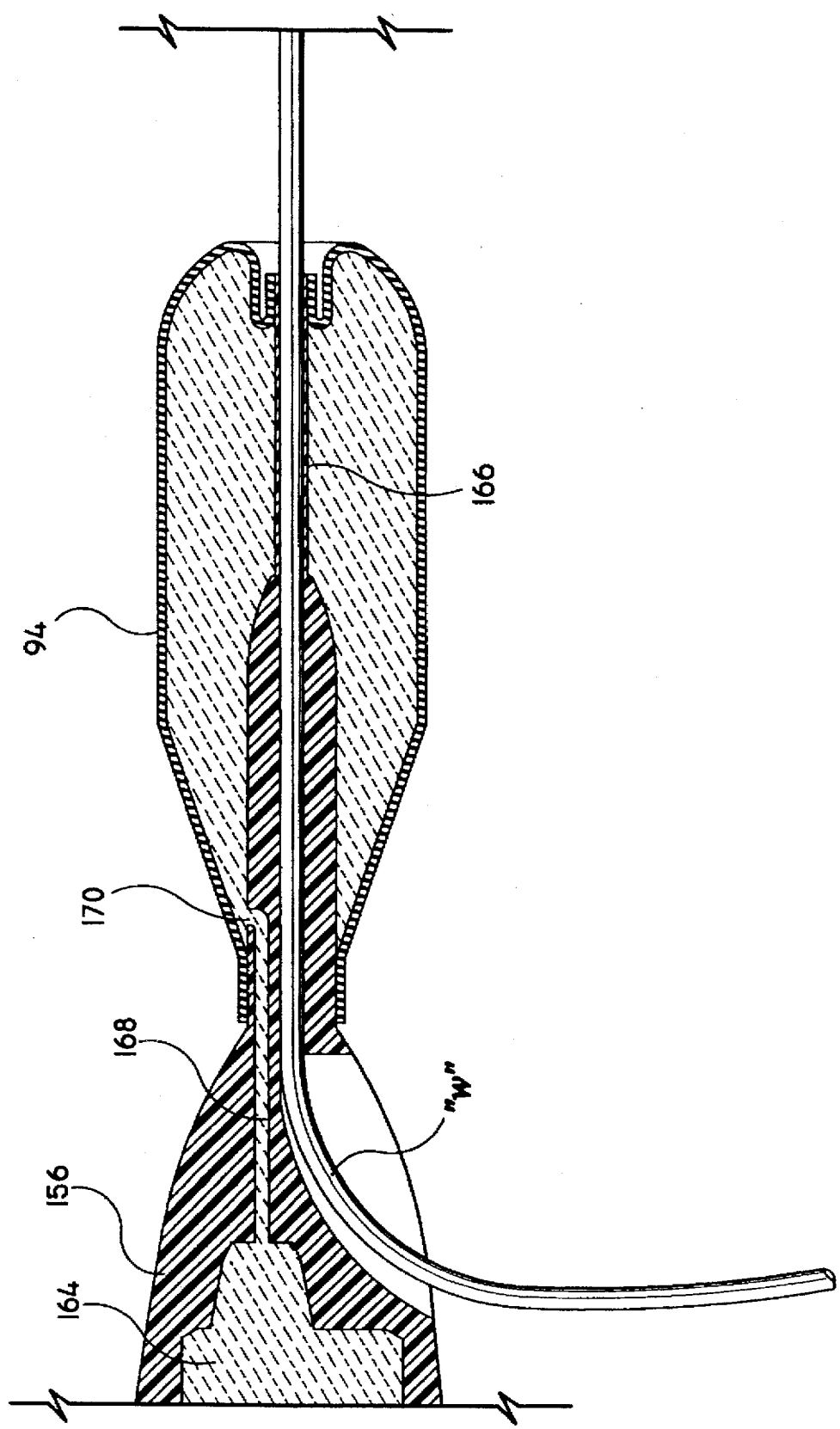
FIG. 21 is an enlarged cross-sectional view of the distal end portion of the elongated portion illustrating the inflatable member in an expanded condition.

Referring now to FIGS. 14-16, there is illustrated the distal end portion of an alternate embodiment of the surgical apparatus of FIG. 1. The handle unit of this embodiment is identical to the handle unit described in connection with FIG. 1. However, in accordance with this embodiment, the inner tube 82 of elongated member 14 is removed and replaced with a guide tube 100. Guide tube 100 is preferably coaxially mounted within outer tube 102 and may be contiguously formed therewith. Guide tube 100 terminates at its proximal end in opening 104 which extends through the outerwall of outer tube 102 to permit feeding of the guide wire "w" during use of the apparatus. Outer tube 102 includes two opposed inflation apertures 106 to permit passage of the inflation fluid from the inflation lumen 108 defined within the interior of outer tube 102 to inflatable member 110.

In further accordance with this embodiment, a unique mounting mechanism is utilized to mount inflatable member 110 in a fluid tight manner about outer tube 102. In particular, outer tube 102 includes a proximally positioned circumferential groove 112 which accommodates first end portion 110a of inflatable member 110 to longitudinally fix the inflatable member 110 at this position. As noted above, the bore of inflatable member 110 is preferably approximates the outer diameter of outer tube 102 defined at circumferential groove 112 such that the material of the inflatable member 110 deforms and stretches when mounted on the outer tube 102, thus, forming a fluid tight seal at this juncture. As described above in connection with FIG. 6A, mounting sleeves 98 may also be used to secure inflatable member 110 to outer tube 102 of this location.

The second end portion 110b of inflatable member 110 is secured to outer tube 102 by plug member 114. In particular, plug member 114 is positioned within the longitudinal bore of outer tube 102 to engage end portion 110b which is at least partially folded back within the longitudinal bore. Plug member 114 includes four projecting members 116 extending radially outwardly from the outer surface of the plug member 114. Projecting members 116 are received within correspondingly dimensioned openings 118 formed in the outer surface of outer tube 102 to positively mount plug member 114 to the outer tube 102. As shown in the Figs., in the mounted position of plug member 114, end portion 110b of inflatable member 110 is wedged between the outer surface of the plug member 114 and the inner surface of outer tube 102, thus, creating a fluid tight seal. Plug member 114 also includes a distal head portion 120 which also engages end portion 110b of inflatable member 110 to wedge the end portion 110b between the plug 114 and the distal end face 122 of outer tube 102. Plug member 114 further includes a longitudinal bore 102 for reception and passage of guide wire "w". The apparatus of FIGS. 12–14 operates in a similar manner to the apparatus of FIG. 1.

Referring now to FIGS. 17–21, there is illustrated an alternate embodiment of the apparatus of FIG. 1. Apparatus 150 is similar in construction to apparatus 10 of FIG. 1 and includes handle unit 152 and elongated member 154 extending distally from the handle unit 152. Handle unit 152 is substantially identical to handle unit 12 of apparatus 10 of FIG. 1 except that the unit 152 further includes a coil spring 155. Coil spring 155 is connected to the rear end portion of trigger 22 at one end and housing 16 at its other end and serves to normally bias the trigger 22 to pivot about pivot pin 28 to its unactuated position depicted in FIGS. 17 and 19.

Nose hub 156 of apparatus 150 includes a filling port generally identified as reference numeral 158. Filling port 158 includes a filling member 160 which is pivotally mounted to nose hub 156 about pivot pins 162. Filling member 160 pivots between an open position to permit the loading of inflation fluid into chamber 164 of nose hub 156 and a closed position. The remaining components of handle unit 152 are substantially identical to their corresponding components of the apparatus of FIG. 1.

Elongated member 154 is integrally connected to nose hub 156 to form a single unit as shown. Elongated member 154 includes an axial bore 166 (FIG. 19) extending therethrough which terminates in a lower surface of nose hub 156. Axial bore 166 is dimensioned for reception of guide wire "w" during use of the apparatus. An inflation lumen 168 extends from inner chamber 164 and partially along the length of elongated member 154. Inflation lumen 168 terminates in distal opening 170 (FIG. 21), thus, fluidly connecting chamber 164 and the interior of inflatable member 94 to permit the dispensing of inflation fluids into the inflatable member 94.

It is to be noted that only a portion of inflatable member 94 is mounted about elongated portion 154. This provides flexibility when initially maneuvering the inflatable member 94 within the tracheal site and also when inflating the member 94 during the tracheostomy procedure. Apparatus 150 is used in a similar manner to apparatus 10.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed is:

1. A surgical apparatus for manipulating body tissue, which comprises:
    a handle member, including:
        a frame having a guide wire channel;
        a self contained fluid dispenser disposed within the frame, the fluid dispenser including a chamber for storing a supply of inflation fluid;
        a curved flexible drive member directly connected to the dispenser; and,
        a trigger moveable relative to the frame and operatively connected to the drive member;
    a generally elongated member connected to the handle member and extending distally therefrom, the elongated member having proximal and distal portions, the elongated member including a longitudinal guide wire passageway in communication with the guide wire channel;
    an inflatable member supported at the distal portion of the elongated member in fluid communication with the fluid dispenser; and,
    an inflation lumen in fluid communication with the chamber and the inflatable member.

2. The surgical apparatus according to claim 1 wherein the elongated member includes an outer tube and an inner tube mounted within the outer tube, the inner and outer tubes defining a space therebetween, the space defining the inflation lumen.

3. The surgical apparatus according to claim 2 wherein the outer tube includes at least one inflation aperture extending through an outer wall thereof in fluid communication with the inflation lumen, the one inflation aperture permitting inflation fluid to pass into the inflatable member to expand the inflatable member.

4. The surgical apparatus according to claim 2 wherein the inner tube is coaxially mounted within the outer tube such that the space defined between the inner and outer tubes is generally annular in cross-section.

5. The surgical apparatus according to claim 2 wherein the inner tube includes a longitudinal bore extending therethrough, the longitudinal bore defining the longitudinal passageway for reception and passage of the guide wire.

6. The surgical apparatus according to claim 1 including a drive member connected at one end thereof to the trigger and at another end thereof to the plunger of the fluid dispenser, the drive member moveable in response to movement of the trigger to cause corresponding reciprocal movement of the plunger within the chamber.

7. The surgical apparatus according to claim 6 wherein the drive member is at least partially accommodated within a guide channel defined in the frame, the drive member reciprocally axially movable within the guide channel.

8. The surgical apparatus according to claim 7 wherein the drive member is contiguously formed with the trigger.

9. The surgical apparatus according to claim 1 wherein the trigger is pivotally mounted to the frame about a pivot pin.

10. The surgical apparatus according to claim 1 wherein the elongated member includes at least one inflation aperture formed in an outer wall thereof and in communication with the inflation lumen, the one inflation aperture permitting passage of the fluid into the inflatable member to expand the inflatable member.

11. The surgical apparatus according to claim 10 wherein the inflatable member is coaxially mounted about the elongated member.

12. The surgical apparatus according to claim 1 including a pressure indicator in communication with the chamber, the pressure indicator actuated when the pressure in the chamber exceeds a predetermined value.

13. The surgical apparatus according to claim 1 wherein the elongated member includes an outer tube and a guide tube positioned within the outer tube, the guide tube defining a bore therein dimensioned for reception and passage of a guide wire therethrough, the guide tube extending to an outer wall of the outer tube at a position intermediate the proximal and distal end portions of the elongated member.

14. The surgical apparatus according to claim 13 wherein the elongated member includes a mounting groove portion, the mounting groove portion defining a cross-sectional dimension which is less than the cross-sectional dimension defined by portions of the elongated member adjacent to said mounting groove portion, the mounting groove portion dimensioned to accommodate an end portion of the inflatable member to retain the inflatable member on the elongated member.

15. The surgical apparatus according to claim 1 including at least one mounting sleeve disposed about the inflatable member for securing the inflatable member about the elongated member.

16. The surgical apparatus according to claim 1 including a filling port accessing the chamber of the fluid dispenser, the filling port permitting loading of inflation fluid into the chamber.

17. The surgical apparatus according to claim 1 wherein the fluid dispenser includes a plunger reciprocally removeable within the chamber for dispensing the inflation fluid.

18. The surgical apparatus according to claim 1 wherein the inflation lumen extends substantially through the whole length of the balloon.

* * * * *